United States Patent [19]
Kobayashi et al.

[11] Patent Number: 5,822,449
[45] Date of Patent: Oct. 13, 1998

[54] TEACHING METHOD AND SYSTEM FOR MOUNTED COMPONENT INSPECTION

[75] Inventors: Shigeki Kobayashi, Kyoto; Norihito Yamamoto, Ohtsu, both of Japan

[73] Assignee: OMRON Corporation, Kyoto, Japan

[21] Appl. No.: 799,986

[22] Filed: Feb. 13, 1997

Related U.S. Application Data

[63] Continuation of Ser. No. 592,626, Jan. 26, 1996, abandoned, which is a continuation of Ser. No. 263,022, Jun. 20, 1994, abandoned, which is a continuation of Ser. No. 166,273, Dec. 13, 1993, abandoned, which is a continuation of Ser. No. 916,420, Jul. 21, 1992, abandoned.

[30] Foreign Application Priority Data

Jul. 22, 1991 [JP] Japan .................................. 3-206272
Jul. 30, 1991 [JP] Japan .................................. 3-214358

[51] Int. Cl.$^6$ ...................................................... G06K 9/00
[52] U.S. Cl. .......................... 382/141; 382/147; 382/149; 348/126
[58] Field of Search .................................. 382/141, 147, 382/150, 149, 159, 160; 348/126, 87

[56] References Cited

U.S. PATENT DOCUMENTS

| | | | |
|---|---|---|---|
| 4,894,790 | 1/1990 | Yotsuya et al. | 358/101 |
| 4,953,100 | 8/1990 | Yotsuya | 348/126 |
| 4,978,224 | 12/1990 | Kishimoto et al. | 356/394 |
| 5,046,113 | 9/1991 | Hoki | 382/147 |
| 5,058,178 | 10/1991 | Ray | 382/8 |
| 5,086,477 | 2/1992 | Yu et al. | 382/145 |
| 5,134,575 | 7/1992 | Takagi | 382/147 |
| 5,134,665 | 7/1992 | Jyoko | 382/8 |
| 5,245,671 | 9/1993 | Kobayashi et al. | 382/141 |

FOREIGN PATENT DOCUMENTS 0 355 377 A1   2/1990   European Pat. Off. .
35 06237 A1    9/1986   Germany .

OTHER PUBLICATIONS

Mengel, "Automated inspection of solder joints on PC boards by supplementary processing of 3D and gray–level images", IECON'90, Nov. 27–30, 1990, pp. 786–791.

Hidde and Prusak, "The use of artificial intelligence for printed circuit board manufacturing"; Computers in Industry, vol. 16, No. 1, (1991).

Park and Tou, "A solder joint inspection system for automated printed circuit board manufacturing", 1990 IEEE International Conference on Robotics and Automation, May 13–18, 1990; pp. 1290–1295.

Driels, "Automatic Defect Classification of Printed Wiring Board Solder Joints"; IEEE Transactions on Components, Hybrids and Manufacturing Technology; vol. 13, No. 12, (1990), pp. 331–340.

Kobayashi et al., "Identifying Solder Surface Orientation From Color Highlight Images"; IECON'90, Nov. 27–30, 1990, vol. I, pp. 822–825.

Patent Abstracts of Japan No. JP62180249.
Patent Abstracts of Japan No. JP62180251.
Patent Abstracts of Japan No. JP62203287.

*Primary Examiner*—Kim Yen Vu
*Assistant Examiner*—Kimberly A. Williams
*Attorney, Agent, or Firm*—Morrison & Foerster LLP

[57] ABSTRACT

An operator actuates keyboard (22) to register board name of a board for teaching (ST11), sets a reference board (1S) on a Y-axis table unit (4) to actuate a start key (ST12), inputs reference points of the reference board (1S) to be set to an original position (ST13), takes a picture of a predetermined area on the reference board to teach a mounting position (ST14), and reads data about component image and its decision criteria of the corresponding component from a component kind table (19) to be stored as teaching data (ST15). This operation is repeatedly executed until all components are taught to a mounted component inspection device which inspects mounting qualities of a plurality of components mounted on an inspected board.

8 Claims, 11 Drawing Sheets

FIG. 2
|  | GOOD SOLDERING | COMPONENT OMISSION | POOR SOLDERING |
|---|---|---|---|
| SECTIONAL VIEW |  |  |  |
| IMAGE PICKUP PATTERN |  |  | 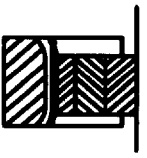 |
| RED COLOR PATTERN |  |  |  |
| GREEN COLOR PATTERN |  |  |  |
| BLUE COLOR PATTERN |  | 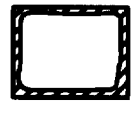 |  |

FIG. 4

| AComp. | BComp. | CComp. | DComp. | EComp. | FComp. | GComp. |
|--------|--------|--------|--------|--------|--------|--------|
| A1Comp. | B1Comp. | C1Comp. | D1Comp. | E1Comp. | F1Comp. | G1Comp. |
| A2Comp. | B2Comp. | C2Comp. | D2Comp. | E2Comp. | F2Comp. | G2Comp. |
| A3Comp. | B3Comp. | C3Comp. | D3Comp. | E3Comp. | F3Comp. | G3Comp. |
| A4Comp. | B4Comp. | C4Comp. | D4Comp. | E4Comp. | F4Comp. | G4Comp. |
| A5Comp. | B5Comp. | C5Comp. | | | F5Comp. | G5Comp. |
| A6Comp. | B6Comp. | C6Comp. | | | F6Comp. | G6Comp. |
| A7Comp. | B7Comp. | C7Comp. | | | | G7Comp. |
| A8Comp. | B8Comp. | C8Comp. | | | | G8Comp. |

| COMP. MODEL | MAKER | LIBRARY NAME |
|---|---|---|
| A | a | RB1068 |
| B | a | RB1068 |
| C | b | RW1608 |
| D | b | RY1608 |
| | | |
| | | |

TEACHING METHOD AND SYSTEM FOR MOUNTED COMPONENT INSPECTION

This application is a file wrapper continuation of U.S. application Ser. No. 08/592,626, filed Jan. 26, 1996; which is a file wrapper continuation of U.S. application Ser. No. 08/263,022, filed Jun. 20, 1994, which is a file wrapper continuation of U.S. application Ser. No. 08/166,273, filed Dec. 13, 1993, which is a file wrapper continuation of U.S. application Ser. No. 07/916,420, filed Jul. 21, 1992, all now abandoned.

BACKGROUND OF THE INVENTION

1. Field of the Invention

This invention relates to a system or method for inspecting a plurality of electronic components mounted on a board such as printed circuit board, the existence and positions of electronic components before soldering and the soldering results after soldering, and more particularly to an improved system or method for teaching mounted component inspection data to a mounted component inspection device to inspect a plurality of components mounted on a board about the mounting condition whether they are good or bad (hereinafter called as ("mounting quality").

2. Discussion of the Related Art

A naked eye inspection is commonly employed to inspect mounted components on an inspected board as to their mounting qualities (hereinafter, the word "mounting" or "mounted" is used to mean it before and after soldering). This naked eye inspection, however, cannot prevent making an inspection mistake and uneven inspection results by inspectors, and is limited about its inspection processing capability.

Recently, there has been proposed a mounted component inspection device which automatically inspects a mounting quality of a base mounted with many components by employing a picture processing technique. The mounted component inspection device is required to be taught prior to its use for each kind of inspected boards in which address, which components and how to be mounted on the boards. This operation is called as "teaching", and the mounted component inspection data includes information relating to pictures and decision criteria for automatic inspection in addition to positions and kinds of components mounted on the inspected board.

The information relating to pictures and decision criteria includes data (shape, length, width and so forth) of a land on a board soldered with each component, data (shape, scale, and so forth) of a window defined as an inspection area, data (hue, brightness and so forth) of characteristic parameters representing soldered condition on the land, and decision criteria for determining whether or not the characteristic parameters are good.

The above-mentioned mounted component inspection data are manually entered into the mounted component inspection device by an operator for each kind of the inspected boards, and has the disadvantages that it consumes much labor and time and the inspection by the device cannot be performed during teaching operations. The positions and kinds of components in the mounted component inspection data to be mounted on the inspected board may use data obtained from a chip mounter or CAD (computer-aided design). The data of picture and decision criteria, however, are required to be taught to the mounted component inspection device for each kind of boards by a manual entry after conveying the reference board properly mounted with the respective components to the device, producing pictures of the respective components and their peripherals to extract the above-mentioned characteristic parameters, and determining the decision criteria.

SUMMARY OF THE INVENTION

It is, therefore, a primary object of this invention to provide an improved method or system for teaching mounted component inspection data, particularly data about pictures and their decision criteria which conventionally consume much labor and time, to a mounted component inspection device.

It is further object of this invention to provide an improved method or system for efficiently and quickly making teaching data without exclusively using a mounted component inspection device.

According to this invention, there is provided a method for teaching mounted component inspection data to a mounted component inspection device to inspect the respective mounting qualities of a plurality of components mounted on a board including the steps of previously storing data about pictures and decision criteria into a storage as the mounted component inspection data for each kind of the components, reading the stored data about the pictures and decision criteria of the components corresponding to the respective components on the board for teaching, and teaching the read data to the mounted component inspection device. The data about pictures and decision criteria necessary for mounted component inspection data are stored prior to teaching, and on a teaching mode the stored data are read out from the storage to be taught to the mounted component inspection device, so that labor and time for teaching the device is extremely reduced.

According to other aspect of this invention, there is provided a method for making teaching data to be taught to a mounted component inspection device to inspect the respective mounting qualities of components mounted on an inspected board, the teaching data being made by corresponding and composing the externally available data about the inspect board with the previously prepared inspection data. The data about the inspected board is externally obtained, the data about inspection are previously prepared, and the inspection data is made by composing the both data, so that the instruction data is made by computer's process without using manual entry operation.

BRIEF DESCRIPTION OF THE DRAWINGS

These and other objectives and advantages of this invention will be more readily apparent from the following detailed description provided in conjunction with the following figures, of which:

FIG. 2 is a table illustrating relations between soldering condition and patterns taken by a camera of FIG. 1;

FIG. 4 illustrates contents of the component kind table;

DETAILED DESCRIPTION OF THE INVENTION

Figure 1:
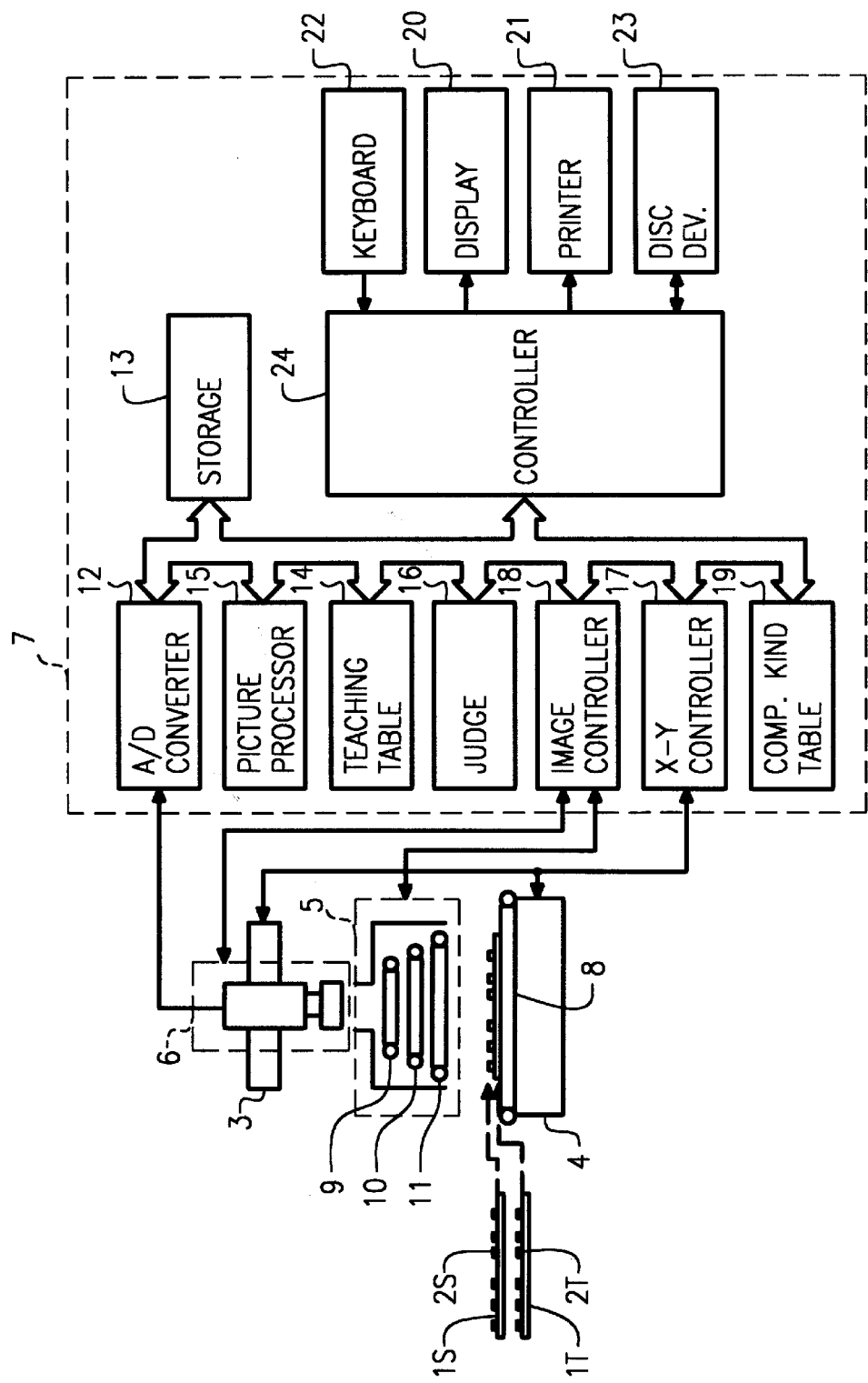
FIG. 1 is a schematic block diagram of a mounted component inspection device applicable to a first embodiment of this invention.

Referring, now, to FIG. 1, there is shown a schematic block diagram of a mounted component inspection device to be applied by a method according to a first embodiment of this invention. The device includes a X-axis table unit 3, a Y-axis table unit 4, a projector 5, a camera 6, and a control processor 7, and is designed to compare characteristic parameters of the respective components 2S mounted on an inspection area of a reference board 1S which are obtained by taking a picture of the board 1S with characteristic parameters of the respective component 2T mounted on an inspection area of an inspected board 1T which are obtained by taking a picture of the board 1T to inspect mounting qualities of the respective components 2T.

The X-axis table unit 3 and Y-axis table unit 4 are provided with motors (not shown in drawings) actuated by a control signal generated from the control processor 7 so that the X-axis table unit 3 moves camera 6 in a X direction and the Y-axis table unit 4 moves a conveyer 8 supporting boards 1S and 1T in a Y direction.

The projector 5 consists of three circular ring light sources 9, 10 and 11 which have different diameters and respectively project red color light, green color light and blue light color light simultaneously in response to the control signal from the processor 7. The light sources 9, 10 and 11 are positioned to have a center right above an observation position by respectively different elevation angles from the observation position. The light sources 9, 10 and 11 respectively have red, green and blue colored transparent plates covering white light sources in this embodiment, but may employ three circular ring colored fluorescent lamps or neon tubes respectively projecting red, green and blue light.

In order to find information (component number, polarity, color code and so forth) and pattern information (various marks) of components on boards 1S and 1T under light by the projector 5, the light sources 9, 10 and 11 are designed to provide a complete white light when their hues are mixed. The light sources 9, 10 and 11 are designed to respectively project lights having red light spectrum, green light spectrum and blue light spectrum each so having a contrast wavelength luminous energy distribution to provide white light when the three color light rays are mixed, and the light volume of the respective hue light is adapted to be adjusted by a camera controller 18 so that white light is obtained by mixing red light, green light and blue light projected from the sources 9, 10 and 11.

The camera 6 employs a color television camera in this embodiment, and is positioned right above the observation position in a downward direction. Thus, reflected lights from the surface of boards 1S and 1T to be inspected are taken by camera 6 to be converted into color signals R, G and B of three primary colors to be provided to control processor 7.

The control processor 7 includes an A/D converter 12, a storage 13, a teaching table 14, a picture processor 15, a judging unit 16, X-Y table controller 17, an image pickup controller 18, a component kind table 19, a display 20, a printer 21, a keyboard 22, a floppy disk driver 23, and a controller 24. On a teaching mode, the component kinds previously stored in component kind table 19 corresponding to components 2S mounted on reference board 1S are read out, and characteristic parameters such as hue and brightness about an inspection area of the respective components 2S on the reference board 1S are applied to make a decision data file. On an inspection mode, color signals R, G and B about the inspected board 1T are processed, and the respective red, green and blue hue patterns are detected about an inspection area of the respective components 2T on the inspected board 1T to produce an inspected data file. The inspected data file is compared with the decision data file, and in view of the comparison results, mounting qualities such as soldering condition about the components 2T on the inspected board 1T are automatically judged.

FIG. 2 is a table showing sectional views of soldering 25, image pickup patterns, red color patterns, green color patterns and blue color patterns taken by camera 6 in a soldering condition—good soldering, component omission and poor soldering. Since apparent difference is found between hue patterns in the table, it become possible to judge the existence of components and soldering condition.

Returning to FIG. 1, the A/D converter 12 converts color signals R, G and B from camera 6 into digital signals to be applied to controller 24. Storage 13 employs RAM, and serves a working area for controller 24. The picture processor 15 performs picture processing about picture data provided through controller 24 to make the inspected data file and the data file for application to controller 24 and judging unit 16.

The component kind table 19 previously stores the data about pictures and decision criteria necessary for mounted component inspection for each kind of the component, such as data about a land on a board soldered with the components (shape, length, width and so forth), data about a window defined as an inspection area (shape, scale and so forth), data about characteristic parameters representing soldering condition on the land (hue, brightness and so forth), and decision criteria for determining whether or not the characteristic parameters are good. When the above-mentioned decision data file is made, the data stored in the table 19 is selected and read out in accordance with kinds of components. The data about pictures in this embodiment is about color pictures, such as hues, brightness (total brightness of all colors, brightness for each hue, saturation or the like which are selectively employed. If the data about pictures is about monochrome, shading data of black and white is employed.

If the controller 24 applies decision data file to the teaching table 14 in a teaching mode, the table 14 stores the decision data file to be read out for application to the judging unit 16 by the controller 24 when the controller 24 in an inspection mode requests table 14 to transmit the stored decision data file to the unit 16. The judging unit 16 compares the decision data file applied from controller 24 in the inspection mode with the inspected data file applied from the picture processor 15 to judge whether soldering condition of each component 2T on the inspected board 1T is good or bad, and sends the judgement results to controller 24. The image pickup controller 18 includes an interface for connecting controller 24 with projector 5 and camera 6, and controls in response to outputs therefrom the respective light sources 9 through 11 of projector 5 to adjust quantity of their light and the camera 6 to keep a mutual balance among the respective hues of light outputs therein. The X-Y table controller 17 includes an interface for connecting controller 24 with X-axis table unit 3 and Y-axis table unit 4 to control the units in response to outputs from controller 24. The display 20 displays on its display panel data of pictures, inspection results, key input and so forth when the data is applied to the display. When an inspection result is applied to printer 21 from controller 24, the printer prints out it in a predetermined format. The keyboard 22 includes various kinds of keys for entry of data about operation, reference board 1S and inspected board 1T, and key entry data is applied to controller 24. The controller 24 includes a micro processor, and controls the operations of making the component kind table 19, teaching, and executing the mounted component inspection device according to the sequences of FIGS. 3, 5 and 6.

Figure 3:
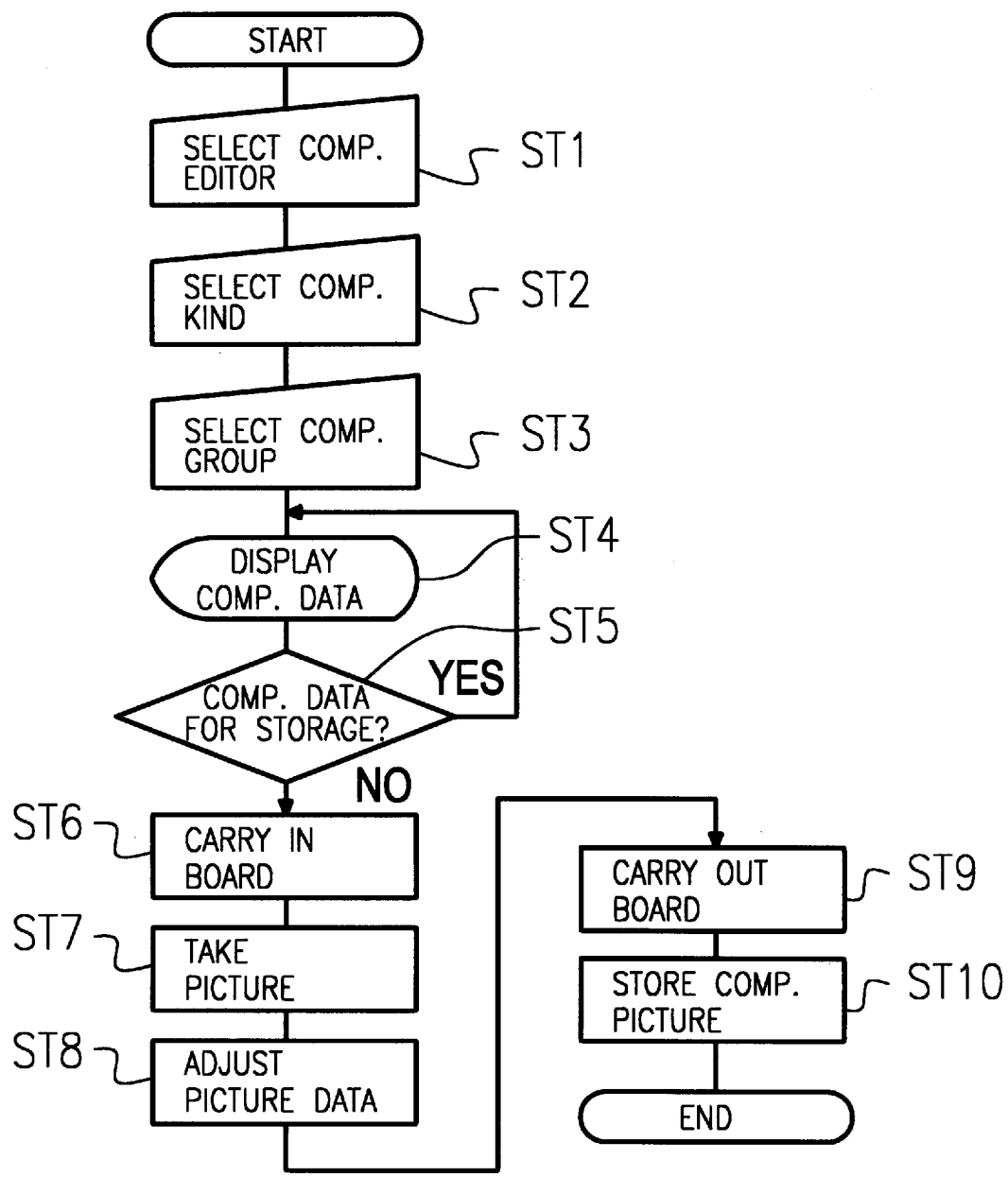
FIG. 3 is a flow chart for making a component kind table.

In FIG. 3, there is shown a sequence for making the component kind table 19. In an initial step "START", the controller 24 actuates projector 5 and camera 6 by controlling the respective components to prepare image pickup condition and data processing condition.

If an operator actuates keyboard 21 to select a component editor in a step ST1, the contents of component kind table 19 previously stored in the mounted component inspection device are displayed by the display 20 as exemplarily shown in a table of FIG. resistor, IC and so forth) represented by refrence letters "A" through "G" and the component groups (ex. 4 which shows a plurality of component kinds (ex. A1 through A8) belonging to the respective component kinds. The operator selects a component kind corresponding to a component for an object from the component kind table in a step ST2, and a corresponding component in the component group of the component kind in a step ST3, so that previously stored component data about the selected component is displayed on display 20 in a step ST4.

If the operator judges the displayed data is useful in automatic inspection even if it is stored, a "YES" reply is produced in an inquiry step ST5 for its succeeding component group evaluation and moves to step ST4. If the operator judges the displayed data cannot be used in automatic inspection, the step ST5 produces a "NO" reply for application to a step ST6 in which the reference board 1S is carried into an observation position of the mounted component inspection device.

In a step ST7, a picture of the corresponding component 2S on reference board 1S is taken by camera 6 to extract parameters of the taken picture. In a step ST8, values of the parameters are adjusted to produce picture data and its decision criteria to be stored in the component kind table 19. The adjusted parameters include positions of components, data of lands, data about windows for bridge detection, data about characteristic parameters representing soldering condition on lands, and decision criteria for determining whether mounting quality is good or bad.

Upon completion of this adjustment, the reference board 1S is carried out from the mounted component inspection device in a step ST9, and newly adjusted component picture data is stored in the component kind table 19 in a step ST10.

Thus, in a same manner, component data about other components for automatic inspection is subsequently stored into component kind table 19.

Figure 5:
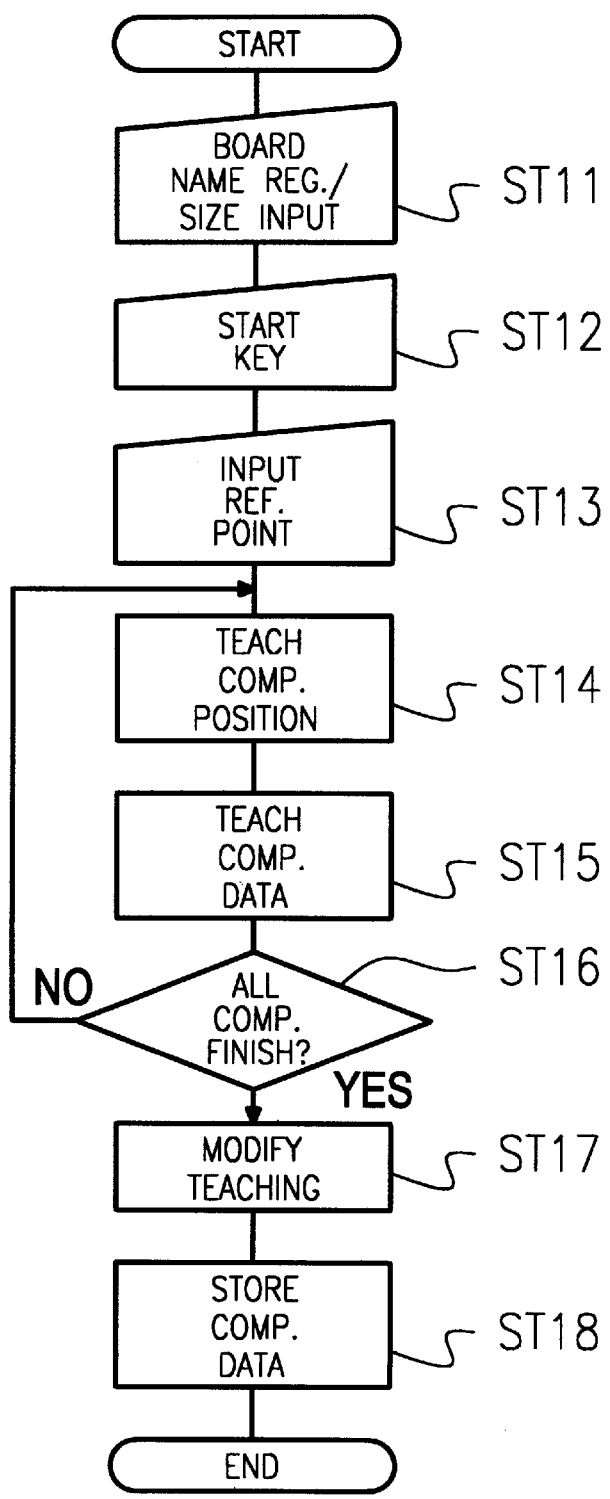
FIG. 5 is a flow chart showing a sequence of teaching.

In FIG. 5, there is shown a sequence for teaching. The operator actuates keyboard 22 to register board name and key-input board size as teaching object in a step ST11, and sets reference board 1S on Y-axis table unit 4 for depressing a start key in a step ST12. In a step ST13, the camera 6 takes a picture of the reference board 1S at its original position and both its right above and left bottom corners to input the size of actual reference board 1S by the reference points, and the controller 24 controls X-axis table unit 3 and Y-axis table unit 4 to bring the reference board 1S to its original position. The reference board 1S has a good mounting quality in which a predetermined component 2S is properly soldered at a component mounting position. If the reference board 1S is fixed at the initial position, the camera 6 takes a picture of a field on reference board 1S to teach a mounting position of a component in a step ST14.

In a step ST15, the contents of component kind table 19 are displayed on display 20, a component corresponding to the component 2S whose mounting position is taught is chosen, and its component data is read out from component kind table 19 to be stored as teaching data.

If same sequence is repeatedly executed about all components on the reference board 1S, a replay "YES" is produced from a step ST16 inquiring if sequences for all components are finished, and applied to a step ST17 to modify teaching. This teaching modification is executed to actually advance automatic inspection about all portions to be inspected by teaching data produced in steps 14 and 15 and to modify only the teaching data of an improper portion if the improper portion is found as the results of the automatic inspection. If a satisfactory result is obtained by the modified teaching data, it is stored as teaching data in a step ST18.

Figure 6:
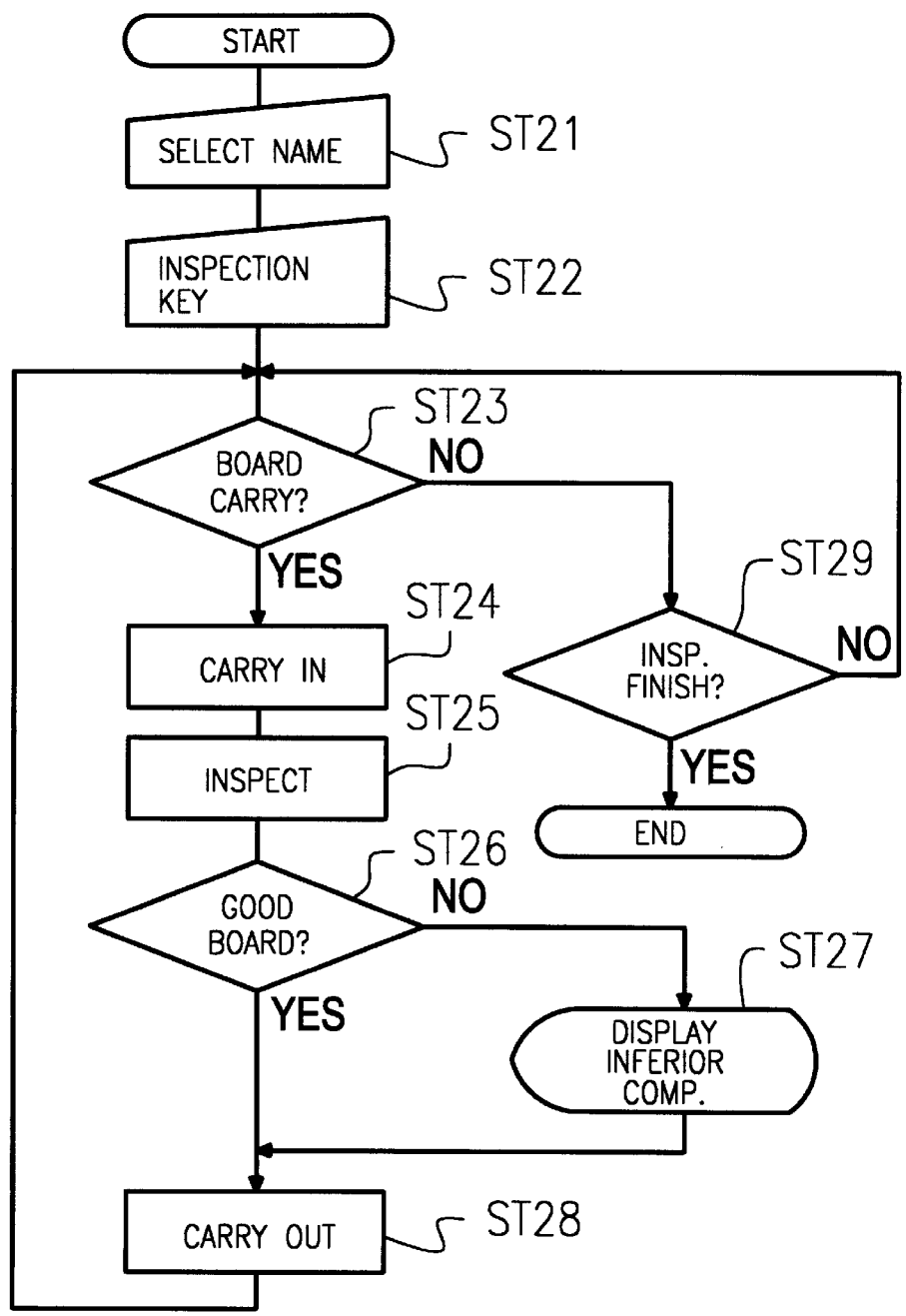
FIG. 6 is a flow chart showing a sequence of an automatic inspection.

In FIG. 6, there is shown a sequence for automatic inspection. In steps ST21 and ST22, name of a board to be inspected is selected and an inspection key is actuated to execute board inspection. In a step ST23, it is inquired if an inspected board 1T is supplied to the mounted component inspection device or if the board is to be carried in. If a replay "YES" is made in the step ST23, conveyer 8 is actuated to carry the inspected board 1T in Y-axis table unit 4 in a step ST24 and automatic inspection is initiated in a step ST25.

In the step ST25, the controller 24 controls the X-axis and Y-axis table units 3 and 4 to fix a view of camera 6 to the first component 2T on the inspected board 1T for taking pictures, the respective land fields in an inspection field are automatically extracted, characteristic parameters in the respective land fields are computed, and an inspected data file is made. Subsequently, the controller 24 applies the inspected data file to the judging unit 16 to compare the inspected data file with the judging data file from teaching table 14 for judging mounting quality of the first component 2T such as soldering condition (step ST26). Thus inspection is repeatedly executed about all components 2T on the inspected board 1T.

If any inferior component such as poor soldering is found as a result of the above-mentioned inspection, the inferior component and its inferior or bad data is displayed on the display 20 or printed by printer 21 (step ST27), the inspected board 1T is carried out from the observation position (step ST28).

If this inspection operation is executed or finished about all inspected boards 1T, a response "YES" is produced in a step ST29 and this inspection sequence is finished.

Thus, according to this embodiment, the data of pictures and inspection criteria for mounted component inspection data is previously stored in a storage for each kind of components, and in a teaching mode the data of pictures and decision criteria about components corresponding to the respective components on a board is electively read out from the storage to be taught to the mounted component inspection device, so that labor and time for teaching is extremely reduced.

Figure 7:
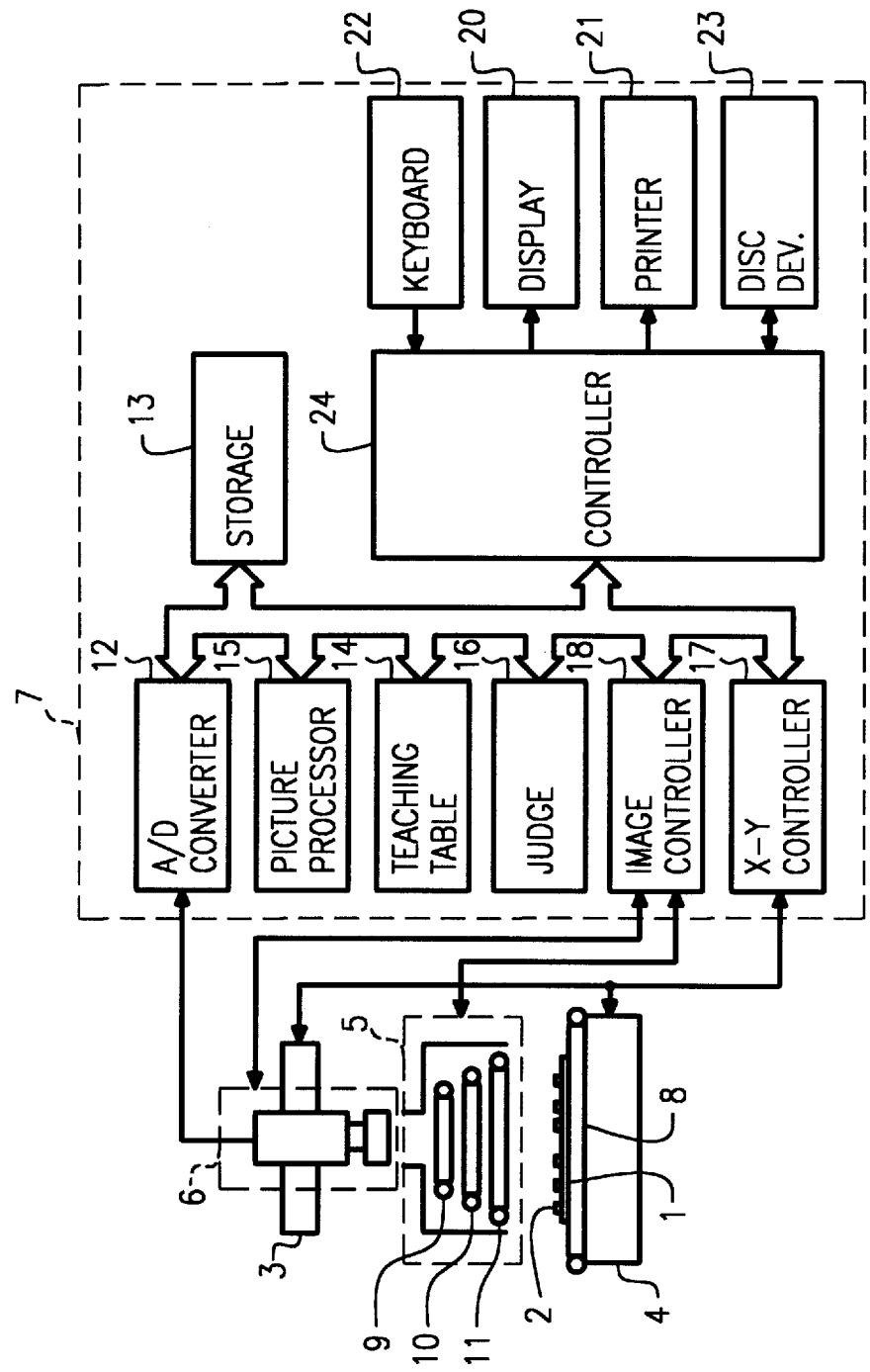
FIG. 7 is a schematic block diagram of a mounted component inspection device applicable to a second embodiment of this invention.

In FIG. 7, there is shown a schematic block diagram of a mounted component device to be taught teaching data in accordance with a second embodiment of this invention. The device of FIG. 7 has a similar construction to that of FIG. 1. The device of FIG. 7 does not include the component kind table of FIG. 1, but its components represented by the same reference numbers as those of FIG. 1 have the same functions or construction as those of FIG. 1. Accordingly, explanation about the same components is omitted for a simplified explanation.

The mounted component inspection device of FIG. 7 is designed to inspect mounting quality of each mounted component 2 on an inspected reference board 1, and includes X and Y axis table units 3 and 4, projector 5, camera 6 and control processor 7. The control processor 7 is designed to compare an inspected data file with decision data file to automatically inspect mounting condition. The processor 7 includes A/D converter 12, storage 13, teaching table 14, picture processor 15, judging unit 16, X-Y table controller 17, image controller 18, display 20, printer 21, keyboard 22, disk driven 23, and controller 24. The disk driver 23 is adapted to be inserted by a floppy disk storing teaching data, controller 24 makes decision data file based on the teaching data to be applied to teaching table 14. The controller 24 reads and writes data with storage 13, and controls operations of the mounted component inspection device.

Figure 8:
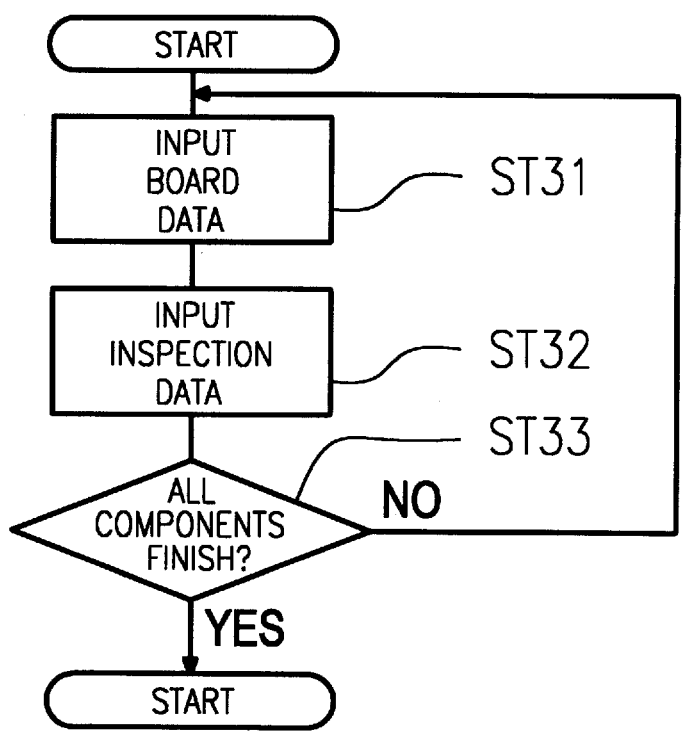
FIG. 8 is a flow chart of making teaching data as the second embodiment.
Figure 9:
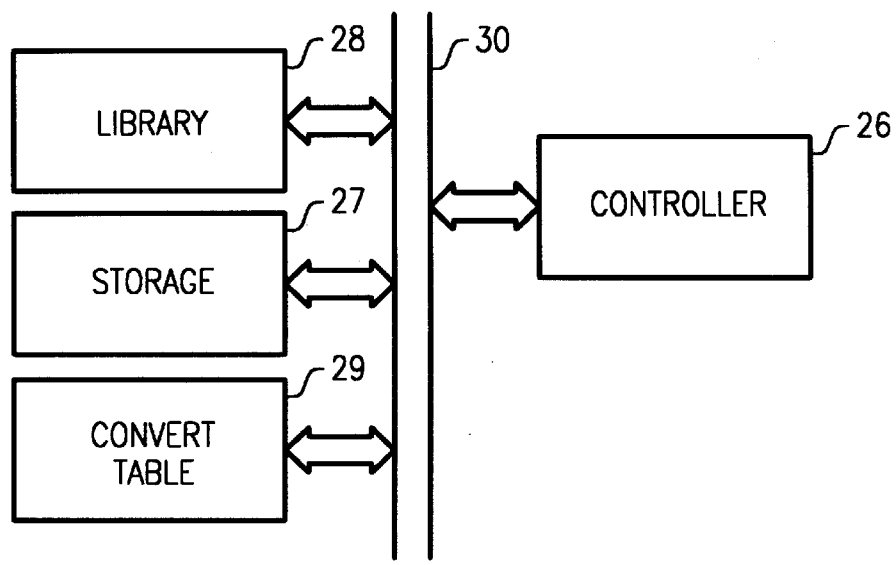
FIG. 9 is a schematic block diagram of a circuit device for executing the flow chart of FIG. 8.

FIG. 8 shows a sequence for making teaching data according to this embodiment, and FIG. 9 shows a part of block diagram of a circuit device for executing the sequence.

The circuit device of FIG. 9 includes a controller 26 employing a microprocessor, and a bus 30 associated with a storage 27, a library 28, and a converting table 29. The storage 27 stores external data about inspected boards such as CAD/CAM data produced in designing and manufacturing boards. The external data includes mounting positions, mounting directions and component models of the respective components, and land's positions and shapes as shown in FIGS. 10 and 11.

Figure 10:
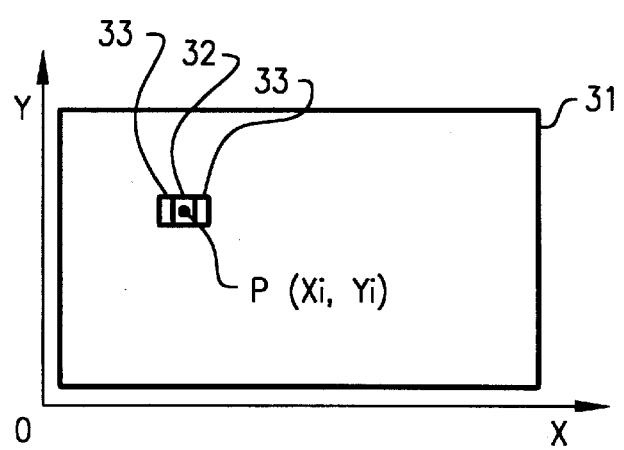
FIG. 10 shows a position of a component on a board.
Figure 11:
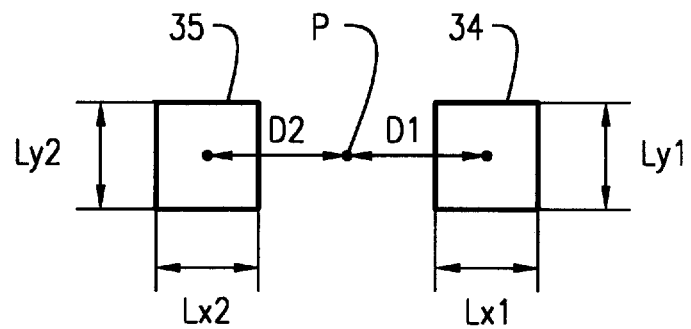
FIG. 11 shows positions and shapes of lands.

In FIG. 10, a chip component 32 is mounted on a board 31 to be inspected, and at a predetermined position P(Xi, Yi) on X-Y coordinates, having its electrodes 33 in a X direction. FIG. 11 shows a pair of lands 34 and 35 to be soldered with the chip component 32 of FIG. 10. The lands 34 and 35 have length Lx1 and Lx2 in a X direction and length Ly1 and Ly2 in a Y direction, forming a rectangular shape. The distances from a position P to lands 34 and 35 are set to $D_1$ and $D_2$. Thus, the above-mentioned external data includes Xi and Yi as data expressing a mounting position, $D_1$, $D_2$, Lx1, Lx2, Ly1 and Ly2 as data expressing positions and shapes of lands 34 and 35. The component models are numbers of kinds, shapes and dimensions of components determined by a component maker. The mounting directions of components are data expressing directions of components with respect to X direction by 90 degree units.

Figure 12:
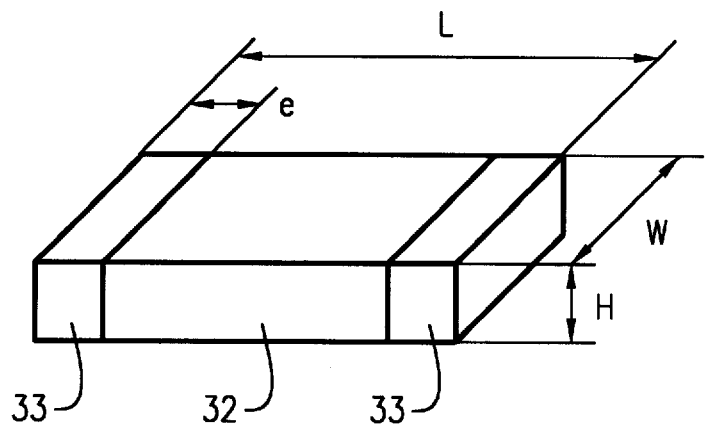
FIG. 12 is a perspective view of showing dimensions of a chip component.
Figures 13, 14:
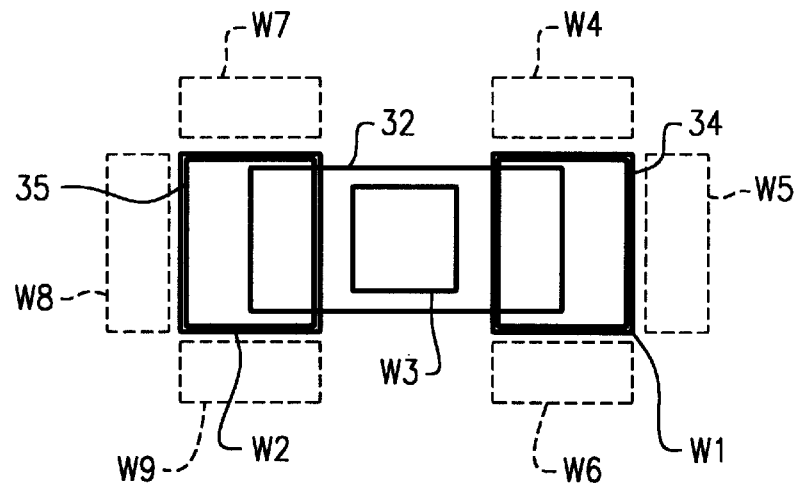
FIG. 13 shows an example of window setting.
FIG. 14 is a converting table employed in the device of FIG. 9.

The library 28 stores library data previously prepared for each component kind regarding inspection. The respective library data have data construction including library name, component kind name, component size, component color, total inspection reference, number of inspection areas, and inspection reference within windows. The component size includes the data of length L, width W and height H of chip component 32, and length e of electrodes 33 thereof as shown in FIG. 12. The component color is color of a body (package) of a component, and includes data of a degree of white, brightness, red hue value, green hue value, and blue hue value. The total inspection reference is reference values for totalizing inspection results within the respective inspection areas (windows) and for deciding quality of inspection result. The number of inspection area is a total number of windows set for each component. As shown in FIG. 13, for instance, the first, second and third windows W1, W2 and W3, if necessary, the fourth through ninth windows W4 through W9, are set for chip component 32. The windows W1 and W2 are provided for judging quality of soldering condition, and set to substantially coincide with shapes and size of lands 34 and 25. The third window W3 is provided for finding any omission of components, and set to a rectangular shape smaller than the external shape of chip component 32 at its mounting position. The windows W4 through W9 are provided for a bridge inspection, and a desired number of windows are set around the lands 34 and 35 according to existence of any components adjacent to the lands. The inspection references within windows are provided in accordance with the number of the above-mentioned windows, and include data about set positions, size, extracting threshold values of areas within windows, and inspection references.

Returning to FIG. 9, the converting table 29 is provided for arranging which inspection data should be employed to process the respective mounting components on a board to be inspected, viz., for arranging which library name's library data in the library 28 should be applied about the external data of the respective mounting components stored in storage 27. FIG. 14 shows an example of the converting table 29, in which components models represented by A, B, C, D . . . for makers correspond to library name represented by "RB1068" and so forth.

The controller 26 arranges corresponding library data of library 28 in view of converting table 29 about the external data of the respective mounting components stored in storage 27 to compose teaching data for storage to the storage 27.

Returning to FIG. 8, a making process of teaching data by controller 26 is shown. In a step ST31, the controller 26 reads out from storage 27 the CAM data about the first mounting component on a board to be inspected such as its mounting position, mounting direction and model name and the CAD data such as positions and shapes of lands to be soldered with the component. Thus, board data is entered. In a step ST32, the controller 26 converts these external data to corresponding library data of library 28 by converting table 29 to compose teaching data for storage to storage 27. Thus, inspection data is entered.

Regarding to subsequent mounting components after the first one, the controller 26 repeatedly executes similar sequence to make teaching data about all components. Accordingly, a reply "YES" is produced in a step ST33, the teaching data making sequence is finished, and the sequence moves to next inspection sequence.

The external data is stored into a floppy disk for application to the mounted component inspection device, and applied to the circuit of FIG. 9.

Thus, according to this embodiment, teaching data is made by allowing the externally available data about a board to be inspected to correspond to the previously prepared data about inspection to be composed, whereby the teaching data can be efficiently made by computer processing without manual input operation. Moreover, the teaching data can be made without exclusively using the mounted component inspection device, so that the device can be used for inspection during making the teaching data. Making the teaching data does not need any expensive teaching machine having an image pickup means, and is perfectly ordered, whereby dispersion of quality of teaching data made by operators is prevented and many advantages are expected.

It should be understood that the above description is merely illustrative of this invention and that many changes and modifications may be made by those skilled in the art without departing from the scope of the appended claims.

What is claimed is:

1. An apparatus for generating data for inspecting components associated with a printed circuit, comprising:
    a first storage means for storing component information, component direction, and component location;
    a second storage means for storing library data having component identifying data and inspection references corresponding to said component identifying data;
    a third storage means for storing a converting table having identifying information corresponding to said library data; and
    a generating means for generating the data for inspecting components using the direction and location of components read from said first storage means, the library data read from said second storage means, and said converting table stored in said third storage means.

2. The apparatus of claim 1, wherein the inspection references comprise information including set positions, size, and extracting threshold values of areas within inspection windows set for inspecting components.

3. The apparatus of claim 1, wherein the identifying information in the converting table comprises library names, component models corresponding to said library names, and component makers of said component models.

4. The method of generating data for inspecting components associated with a printed circuit comprising:
    storing library data and a converting table in a memory, said library data having component identifying data and inspection references corresponding to said component identifying data, and said converting table having component identifying information corresponding to said library data for identifying said components;
    inputting component information, the direction of the components, and the location of the components; and
    generating the data for inspecting the components using he library data, the converting table, the component information, the direction and the location.

5. The method of claim 4, wherein said inspection references comprise information including set positions, size, and extracting threshold values of areas within inspection windows set for said components.

6. The method of claim 4, wherein the component identifying information in the converting table comprises library names, component models corresponding to said library names, and component makers to said component models.

7. A method of teaching data for inspecting components associated with a printed circuit to an apparatus for inspecting components, comprising:
    storing image data of the components and corresponding inspection references to a memory;
    selectively reading a portion of said image data and a corresponding inspection reference from said memory; and
    teaching said portion of said image data and the corresponding inspection reference to said apparatus,
    wherein two or more of said components have the same inspection reference.

8. The method of claim 7, wherein said corresponding inspection references comprise information including set positions, size and extracting threshold values of areas within inspection windows set for said inspection components.

* * * * *